(12) United States Patent  (10) Patent No.: US 9,125,586 B2
Yao  (45) Date of Patent: Sep. 8, 2015

(54) CONTINUOUS ACQUISITION AND PROCESSING OF ULTRASOUND COLOR DATA

(75) Inventor: Linxin Yao, Renton, WA (US)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 1580 days.

(21) Appl. No.: 12/359,921

(22) Filed: Jan. 26, 2009

(65) Prior Publication Data

US 2009/0192387 A1 Jul. 30, 2009

Related U.S. Application Data

(60) Provisional application No. 61/023,783, filed on Jan. 25, 2008.

(51) Int. Cl.
*A61B 8/06* (2006.01)

(52) U.S. Cl.
CPC .......................................... *A61B 8/06* (2013.01)

(58) Field of Classification Search
None
See application file for complete search history.

(56) References Cited

U.S. PATENT DOCUMENTS

| | | | | |
|---|---|---|---|---|
| 5,014,710 A * | 5/1991 | Maslak et al. | ................. | 600/441 |
| 5,462,057 A * | 10/1995 | Hunt et al. | ..................... | 600/447 |
| 5,623,928 A * | 4/1997 | Wright et al. | ................. | 600/447 |
| 5,667,373 A * | 9/1997 | Wright et al. | ................. | 600/443 |
| 5,718,230 A * | 2/1998 | Chapman et al. | ............. | 600/453 |
| 5,910,119 A * | 6/1999 | Lin | ................................ | 600/455 |
| 5,976,088 A * | 11/1999 | Urbano et al. | ................ | 600/443 |
| 6,083,168 A * | 7/2000 | Hossack et al. | ............... | 600/443 |
| 6,500,122 B1 * | 12/2002 | Washburn et al. | ............ | 600/443 |
| 6,589,177 B1 * | 7/2003 | Detmer et al. | ................ | 600/443 |
| 6,612,992 B1 * | 9/2003 | Hossack et al. | ............... | 600/467 |
| 6,666,823 B2 * | 12/2003 | Yao | ............................... | 600/443 |
| 7,077,807 B2 * | 7/2006 | Torp et al. | ...................... | 600/438 |
| 2007/0038083 A1 * | 2/2007 | Srinivasan et al. | ............ | 600/437 |
| 2007/0078347 A1 * | 4/2007 | Srinivasan et al. | ............ | 600/465 |

* cited by examiner

*Primary Examiner* — Long V Le
*Assistant Examiner* — Bradley Impink
(74) *Attorney, Agent, or Firm* — Kory D. Christensen; Stoel Rives LLP (57) ABSTRACT

A method displays ultrasound color flow image data in a plurality of output frames by continuously acquiring color flow image data. Each output frame includes a plurality of scan lines that collectively represent a field of view for an ultrasound image. The method includes sequentially transmitting a plurality of ultrasound beams. For each of the transmitted beams, multiple receive beams are formed along respective parallel scan lines. As the sequence progresses, sets of co-linear receive beams are formed along each of the respective scan lines at a predetermined rate both within a particular frame and between successive frames. The method also includes processing the sets of co-linear receive beams along each of the respective scan lines to generate color flow image data corresponding to the respective scan lines, and displaying a color flow image representing the generated color flow image data.

20 Claims, 7 Drawing Sheets

Color Beam Number → 210

| Sq# | A# | 1 | 2 | 3 | 4 | 5 | 6 | 7 | 8 | ... | 37 | 38 | 39 | 40 |
|-----|----|---|---|---|---|---|---|---|---|-----|----|----|----|----|
| 001 | 1  | I |   |   |   |   |   |   |   |     |    |    |    |    |
| 002 | 1  |   | I |   |   |   |   |   |   |     |    |    |    |    |
| 003 | 1  |   |   | I |   |   |   |   |   |     |    |    |    |    |
| 004 | 1  |   |   |   | I ⟵216 |   |   |   |   |     |    |    |    |    |
| 005 | 2  | I |   |   |   |   |   |   |   |     |    |    |    |    |
| 006 | 2  |   | I |   |   |   |   |   |   |     |    |    |    |    |
| 007 | 2  |   |   | I |   |   |   |   |   |     |    |    |    |    |
| 008 | 2  |   |   |   | I |   |   |   |   |     |    |    |    |    |
| ... |    |   |   |   |   |   |   |   |   |     |    |    |    |    |
| 037 | 10 | I |   |   |   |   |   |   |   |     |    |    |    |    |
| 038 | 10 |   | I |   |   |   |   |   |   |     |    |    |    |    |
| 039 | 10 |   |   | I |   |   |   |   |   |     |    |    |    |    |
| 040 | 10 |   |   |   | I |   |   |   |   |     |    |    |    |    |
| 041 | 1  |   |   |   |   | I |   |   |   |     |    |    |    |    |
| 042 | 1  |   |   |   |   |   | I |   |   |     |    |    |    |    |
| 043 | 1  |   |   |   |   |   |   | I |   |     |    |    |    |    |
| 044 | 1  |   |   |   |   |   |   |   | I |     |    |    |    |    |
| 045 | 2  |   |   |   |   | I |   |   |   |     |    |    |    |    |
| 046 | 2  |   |   |   |   |   | I |   |   |     |    |    |    |    |
| 047 | 2  |   |   |   |   |   |   | I |   |     |    |    |    |    |
| 048 | 2  |   |   |   |   |   |   |   | I |     |    |    |    |    |
| ... |    |   |   |   |   |   |   |   |   |     |    |    |    |    |
| 077 | 10 |   |   |   |   | I |   |   |   |     |    |    |    |    |
| 078 | 10 |   |   |   |   |   | I |   |   |     |    |    |    |    |
| 079 | 10 |   |   |   |   |   |   | I |   |     |    |    |    |    |
| 080 | 10 |   |   |   |   |   |   |   | I |     |    |    |    |    |
| ... |    |   |   |   |   |   |   |   |   |     |    |    |    |    |
| 361 | 1  |   |   |   |   |   |   |   |   |     | I  |    |    |    |
| 362 | 1  |   |   |   |   |   |   |   |   |     |    | I  |    |    |
| 363 | 1  |   |   |   |   |   |   |   |   |     |    |    | I  |    |
| 364 | 1  |   |   |   |   |   |   |   |   |     |    |    |    | I  |
| 365 | 2  |   |   |   |   |   |   |   |   |     | I  |    |    |    |
| 366 | 2  |   |   |   |   |   |   |   |   |     |    | I  |    |    |
| 367 | 2  |   |   |   |   |   |   |   |   |     |    |    | I  |    |
| 368 | 2  |   |   |   |   |   |   |   |   |     |    |    |    | I  |
| ... |    |   |   |   |   |   |   |   |   |     |    |    |    |    |
| 397 | 10 |   |   |   |   |   |   |   |   |     | I  |    |    |    |
| 398 | 10 |   |   |   |   |   |   |   |   |     |    | I  |    |    |
| 399 | 10 |   |   |   |   |   |   |   |   |     |    |    | I  |    |
| 400 | 10 |   |   |   |   end of a color frame   |   |   |   |     |    |    |    | I  |
| 401 | 1  | I |   |   |   |   |   |   |   |     |    |    |    |    |
| 402 | 1  |   | I |   |   |   |   |   |   |     |    |    |    |    |
| 403 | 1  |   |   | I |   |   |   |   |   |     |    |    |    |    |
| 404 | 1  |   |   |   | I |   |   |   |   |     |    |    |    |    |
| 405 | 2  | I |   |   |   |   |   |   |   |     |    |    |    |    |
| 406 | 2  |   | I |   |   |   |   |   |   |     |    |    |    |    |
| 407 | 2  |   |   | I |   |   |   |   |   |     |    |    |    |    |
| 408 | 2  |   |   |   | I |   |   |   |   |     |    |    |    |    |
| ... | ...|   |   |   |   | ... |   |   |   |     |    |    |    |    |

| Sq# | A# | 1 | 2 | 3 | ...10 | 11 | 12 | 13 | ...20 | 21 | 22 | 23 | ...30 | 31 | 32 | 33 | ...40 |
|---|---|---|---|---|---|---|---|---|---|---|---|---|---|---|---|---|---|
| 001 | 1 | I | I | I | ...I | | | | | | | | | | | | |
| 002 | 1 | | | | | I | I | I | ...I | | | | | | | | |
| 003 | 1 | | | | | | | | | I | I | I | ...I | | | | |
| 004 | 1 | | | | | | | | | | | | | I | I | I | ...I |
| 005 | 2 | I | I | I | ...I | | | | | | | | | | | | |
| 006 | 2 | | | | | I | I | I | ...I | | | | | | | | |
| 007 | 2 | | | | | | | | | I | I | I | ...I | | | | |
| 008 | 2 | | | | | | | | | | | | | I | I | I | ...I |
| 009 | 3 | I | I | I | ...I | | | | | | | | | | | | |
| 010 | 3 | | | | | I | I | I | ...I | | | | | | | | |
| 011 | 3 | | | | | | | | | I | I | I | ...I | | | | |
| 012 | 3 | | | | | | | | | | | | | I | I | I | ...I |
| 013 | 4 | I | I | I | ...I | | | | | | | | | | | | |
| 014 | 4 | | | | | I | I | I | ...I | | | | | | | | |
| 015 | 4 | | | | | | | | | I | I | I | ...I | | | | |
| 016 | 4 | | | | | | | | | | | | | I | I | I | ...I |
| 017 | 5 | I | I | I | ...I | | | | | | | | | | | | |
| 018 | 5 | | | | | I | I | I | ...I | | | | | | | | |
| 019 | 5 | | | | | | | | | I | I | I | ...I | | | | |
| 020 | 5 | | | | | | | | | | | | | I | I | I | ...I |
| 021 | 6 | I | I | I | ...I | | | | | | | | | | | | |
| 022 | 6 | | | | | I | I | I | ...I | | | | | | | | |
| 023 | 6 | | | | | | | | | I | I | I | ...I | | | | |
| 024 | 6 | | | | | | | | | | | | | I | I | I | ...I |
| 025 | 7 | I | I | I | ...I | | | | | | | | | | | | |
| 026 | 7 | | | | | I | I | I | ...I | | | | | | | | |
| 027 | 7 | | | | | | | | | I | I | I | ...I | | | | |
| 028 | 7 | | | | | | | | | | | | | I | I | I | ...I |
| 029 | 8 | I | I | I | ...I | | | | | | | | | | | | |
| 030 | 8 | | | | | I | I | I | ...I | | | | | | | | |
| 031 | 8 | | | | | | | | | I | I | I | ...I | | | | |
| 032 | 8 | | | | | | | | | | | | | I | I | I | ...I |
| 033 | 9 | I | I | I | ...I | | | | | | | | | | | | |
| 034 | 9 | | | | | I | I | I | ...I | | | | | | | | |
| 035 | 9 | | | | | | | | | I | I | I | ...I | | | | |
| 036 | 9 | | | | | | | | | | | | | I | I | I | ...I |
| 037 | 10 | I | I | I | ...I | | | | | | | | | | | | |
| 038 | 10 | | | | | I | I | I | ...I | | | | | | | | |
| 039 | 10 | | | | | | | | | I | I | I | ...I | | | | |
| 040 | 10 | | | | | | | | | | | | | I | I | I | ...I |
| 041 | 11 | I | I | I | ...I | | | | | | | | | | | | |
| 042 | 11 | | | | | I | I | I | ...I | | | | | | | | |
| 043 | 11 | | | | | | | | | I | I | I | ...I | | | | |
| 044 | 11 | | | | | | | | | | | | | I | I | I | ...I |
| 045 | 12 | I | I | I | ...I | | | | | | | | | | | | |
| 046 | 12 | | | | | I | I | I | ...I | | | | | | | | |
| 047 | 12 | | | | | | | | | I | I | I | ...I | | | | |
| 048 | 12 | | | | | | | | | | | | | I | I | I | ...I |
| 049 | 13 | I | I | I | ...I | | | | | | | | | | | | |
| 050 | 13 | | | | | I | I | I | ...I | | | | | | | | |
| 051 | 13 | | | | | | | | | I | I | I | ...I | | | | |
| 052 | 13 | | | | | | | | | | | | | I | I | I | ...I |
| 053 | 14 | I | I | I | ...I | | | | | | | | | | | | |
| 054 | 14 | | | | | I | I | I | ...I | | | | | | | | |
| 055 | 14 | | | | | | | | | I | I | I | ...I | | | | |
| 056 | 14 | | | | | | | | | | | | | I | I | I | ...I |

Color Beam Number (410); 412; 414; 416

FIG. 7

CONTINUOUS ACQUISITION AND PROCESSING OF ULTRASOUND COLOR DATA

RELATED APPLICATION

This application claims the benefit under 35 U.S.C. §119 (e) of U.S. Provisional Application No. 61/023,783, filed Jan. 25, 2008, which is hereby incorporated by reference herein in its entirety.

TECHNICAL FIELD

This disclosure generally relates to ultrasonic imaging. More specifically, this disclosure relates to continuously acquiring color flow image data and ultrasound color processing.

SUMMARY

This disclosure provides a method for continuously acquiring color flow image data at a predetermined color sample rate for each of a plurality of color beams in a frame. The method receives one acoustic beam for each color beam in a frame within each color pulse repetition time. This continuous color data stream allows for new methods of color processing.

DETAILED DESCRIPTION

Medical ultrasound color flow imaging is a powerful diagnostic tool in many medical areas. For example, medical personnel may use ultrasound color flow imaging for visualizing, in real time, the distribution of blood flow in a specific region of interest.

In one embodiment, a method displays ultrasound color flow image data in a plurality of output frames by continuously acquiring color flow image data. Each output frame includes a plurality of scan lines that collectively represent a field of view for an ultrasound image. The method includes sequentially transmitting a plurality of ultrasound beams. For each of the transmitted ultrasound beams, multiple receive beams are formed along respective parallel scan lines. As the sequence progresses, sets of co-linear receive beams are formed along each of the respective scan lines at a predetermined rate both within a particular frame and between successive frames. As used herein, the term "co-linear" refers to beams that are formed along the same scan line. The method also includes processing the sets of co-linear receive beams along each of the respective scan lines to generate color flow image data corresponding to the respective scan lines, and displaying a color flow image representing the generated color flow image data.

In certain embodiments, forming the plurality of receive beams for each of the transmitted ultrasound beams includes, for a first transmitted ultrasound beam, forming a first predetermined number of receive beams corresponding to a first group of respective parallel scan lines. For a second transmitted ultrasound beam, the method may include forming a second predetermined number of receive beams corresponding to a second group of respective parallel scan lines. The first group of respective parallel scan lines is different than the second group of respective parallel scan lines. Forming the sets of co-linear receive beams may include, for a third transmitted ultrasound beam, forming a third predetermined number of receive beams corresponding to the first group of respective parallel scan lines such that the third predetermined number of receive beams are respectively co-linear with the first predetermined number of receive beams. Similarly, for a fourth transmitted ultrasound beam, the method may include forming a fourth predetermined number of receive beams corresponding to the second group of respective parallel scan lines such that the fourth predetermined number of receive beams are respectively co-linear with the second predetermined number of receive beams.

In certain embodiments, the method may further include determining the number of co-linear receive beams to include in each set for processing after forming the receive beams corresponding to a particular frame based on at least one of time-resolution and sensitivity. In addition, or in other embodiments, the method may include determining, without user intervention, the number of co-linear receive beams to include in each set for processing based on a depth of a point of interest imaged by the plurality of ultrasound beams. The method may also automatically change the number of co-linear receive beams to include in each set for processing so as to maintain a user-selected frame rate.

In certain embodiments, the method also includes overlapping data between the successive frames. At least one receive beam may be processed along with a first set of co-linear receive beams to generate first color flow image data corresponding to a first frame, and along with a second set of co-linear receive beams to generate second color flow image data corresponding to a second frame. Thus, the method may calculate a velocity value, for example, using known correlation routines (for example, first-order delay correlation may suffice) with data from both the first set and the second set. The method may also calculate a velocity spectrum using known techniques such as a fast Fourier transform (FFT) with data from both the first set and the second set. The method may change the number of receive beams from at least one of the first set and the second set that are used to calculate the FFT based on at least one of a time-resolution and a color sensitivity.

The embodiments of the disclosure will be best understood by reference to the drawings, wherein like elements are designated by like numerals throughout. In the following description, numerous specific details are provided for a thorough understanding of the embodiments described herein. However, those of skill in the art will recognize that one or more of the specific details may be omitted, or other methods, components, or materials may be used. In some cases, operations are not shown or described in detail where skilled medical ultrasound engineers will not require such detail to understand how to practice those aspects of the invention.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or Detailed Description is for illustrative purposes only and is not meant to imply a required order, unless specified to require an order.

Figure 1:
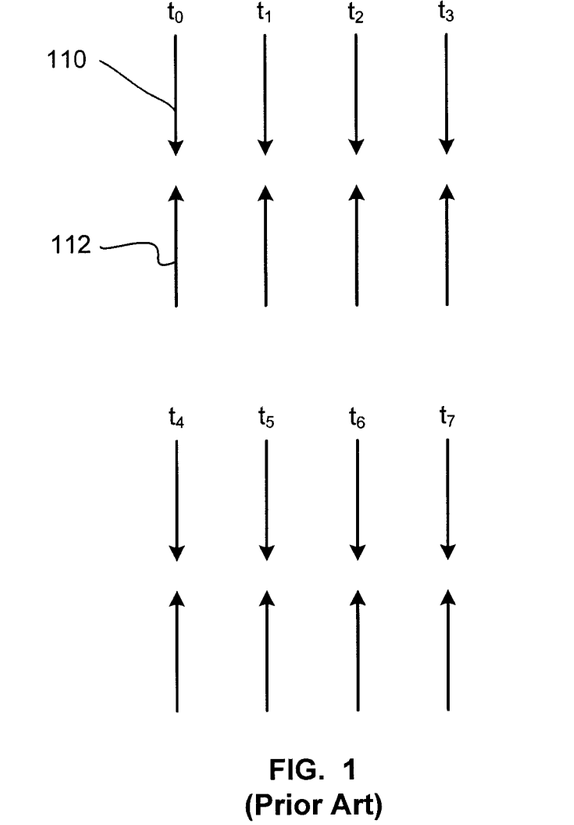
FIG. 1 is a graphical representation of a conventional method for transmitting and receiving acoustic beams to acquire color flow image data.

A conventional method of performing medical ultrasound color flow imaging is generally based on forming color beams, which include color flow image data corresponding to respective receive scan lines in an output frame for display on a monitor. Generally, a packet of acoustic beams is transmitted and received at a same location, under the same settings for a particular color beam. For example, FIG. 1 is a graphical representation of a conventional method for transmitting and receiving acoustic beams. As shown in FIG. 1, a single transmit (Tx) beam 110 is emitted and a single receive (Rx) beam 112 is detected at each sample time $t_0, t_1, t_2, t_3, \ldots, t_7$. Two or more acoustic Tx/Rx beams may correspond to the same packet and are acquired at the same location. For example, the acoustic beams at sample times $t_0$ and $t_4$ may correspond to the same location and be assigned to the same packet (e.g., with a packet size of two) such that they are processed together to determine color flow image data corresponding to a particular color beam or scan line.

The packet size usually includes, for example, four to sixteen Tx/Rx acoustic beams sequentially transmitted and received at a color sample rate. Using a larger packet size generally provides increased color sensitivity. The differences among the Tx/Rx acoustic beams in a packet provide motion or flow information. The packet of acoustic beams is processed (e.g., using first order delay correlation) to detect the average velocity at each depth. Then, a color beam is calculated based on the velocity and other data.

Conventionally, medical ultrasound color flow imaging is based on forming individual color beams one-by-one, or one group of color beams at a time. Generally, the acoustic beams corresponding to a particular color beam in a previous frame are separated in time from acoustic beams for the same color beam in a current frame by several packets of acoustic beams corresponding to other color beams. Therefore, the acoustic beams corresponding to a color beam in the previous frame are no longer useful for calculating the same color beam in the current frame.

The following example demonstrates the sequencing used to collect a frame of color data. The example detects a color flow at a maximum depth of approximately 16 cm. This maximum depth corresponds to a time of approximately 250 μsec needed to obtain the acoustic data. The acoustic pulse repetition frequency (prf) in this example is approximately 4 kHz. This example is also configured to detect a color velocity corresponding to a color prf of 1 kHz (e.g., data corresponding to an Rx beam is added to each packet every 1 msec until the packet is full for a particular frame). Therefore, this example interleaves four color beams.

The color frame in this example includes forty scan lines or color beams. To achieve a desired color sensitivity or resolution, each color beam uses ten acoustic beams at the same location. In other words, the packet size is ten.

The conventional color image data are collected according to the following sequence:

1. Color Beam 1, acoustic beam 1;
2. Color Beam 2, acoustic beam 1;
3. Color Beam 3, acoustic beam 1;
4. Color Beam 4, acoustic beam 1;
5. Color Beam 1, acoustic beam 2;
6. Color Beam 2, acoustic beam 2;
7. Color Beam 3, acoustic beam 2;
8. Color Beam 4, acoustic beam 2;
9 . . . ;
. . .
40. Color Beam 4, acoustic beam 10;
41. Color Beam 5, acoustic beam 1;
42. Color Beam 6, acoustic beam 1;
43. Color Beam 7, acoustic beam 1;
44. Color Beam 8, acoustic beam 1;
45. Color Beam 5, acoustic beam 2;
46. Color Beam 6, acoustic beam 2;
47. Color Beam 7, acoustic beam 2;
48. Color Beam 8, acoustic beam 2;
. . .
360. Color Beam 36, acoustic beam 10;
361. Color Beam 37, acoustic beam 1
362. Color Beam 38, acoustic beam 1;
363. Color Beam 39, acoustic beam 1;
364. Color Beam 40, acoustic beam 1;
. . .
397. Color Beam 37, acoustic beam 10;
398. Color Beam 38, acoustic beam 10;
399. Color Beam 39, acoustic beam 10;
400. Color Beam 40, acoustic beam 10;
401. Color Beam 1, acoustic beam 1 . . .

As shown above, it takes 400 acoustic beams, or 0.1 second to make a color frame as specified in this example. Thus, the color frame rate is ten frames per second.

The $401^{st}$ acoustic beam in this example starts a new frame. Like ten of the acoustic beams in the previous frame (e.g., the $1^{st}$ acoustic beam, the $5^{th}$ acoustic beam, etc.), the $401^{st}$ acoustic beam in the sequence is also at the position of color beam number 1. However, the data acquired in the previous frame will be of little use for the new frame because the $401^{st}$ acoustic beam occurs too late as compared to the acoustic beams corresponding to the color beam number 1 in the previous frame. In other words, because forty acoustic beams are used for each set of four color beams with a packet size of ten, the process repeats ten times at the color prf before acquiring another acoustic beam (e.g., the $401^{st}$ acoustic beam) corresponding to color beam number 1 in the new frame.

Because there is such a large amount of delay in receiving data corresponding to a particular color beam between frames, the data from the previous frame cannot generally be combined with data from the new frame to increase color flow sensitivity and resolution. For example, it may be desirable to average data corresponding to a particular color beam that is acquired at regular intervals (e.g., at the color prf). However, due to the delay between frames in conventional systems, the data from one frame that corresponds to color beam number 1 may not be usable to average with the color flow image data corresponding to color beam number 1 from a previous frame. As another example, accuracy may be increased by using a larger number of data points when filtering (e.g., using a wall filter) to isolate the acoustic echoes caused by moving blood flows from those acoustic echoes produced by tissue or moving vessel walls. However, the discontinuous nature of data acquired from conventional systems limits the number of data points available to wall filters and other signal processing methods.

Figure 2:
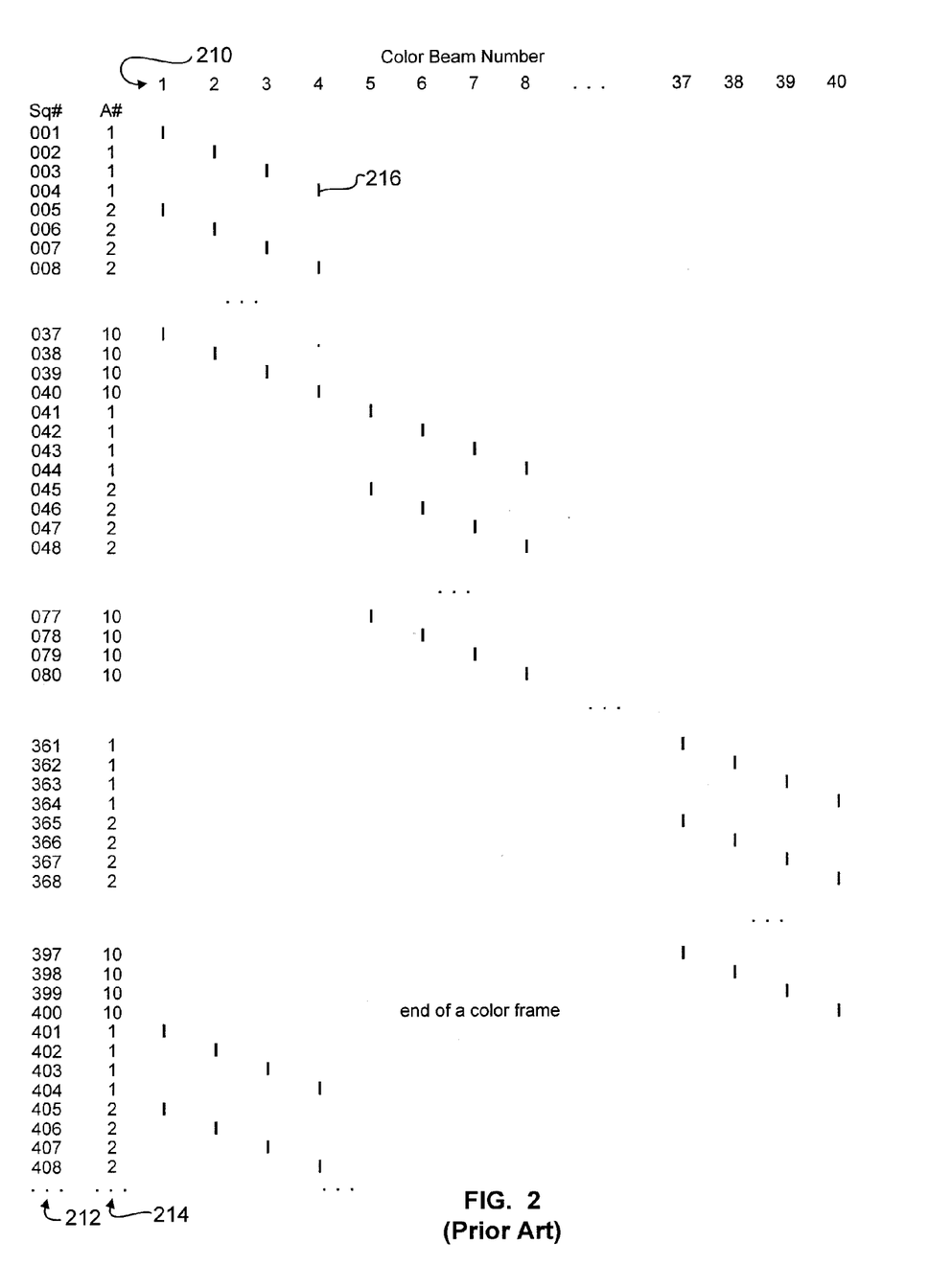
FIG. 2 is a graphical representation of sequencing used in conventional color data acquisition.

FIG. 2 is a graphical representation of sequencing used in conventional color data acquisition. The numbers in the horizontal row 210 represent the color beam numbers (e.g., corresponding to scan lines) in a frame, which range from 1 to 40 in this example. The first column 212 represents a sequencing number (e.g., corresponding to sequential Tx/Rx acoustic beams). The second column 214 represents the acoustic beam number in a packet. The lines 216 in the various rows and columns represent acquired acoustic data corresponding to respective sequence numbers and color beam numbers.

For example, data acquired during sequence number 1 corresponds to color beam number 1, data acquired during sequence number 2 corresponds to color beam number 2, data acquired during sequence number 3 corresponds to color beam number 3, and data acquired during sequence number 4 corresponds to color beam number 4. As discussed above, this example interleaves four color beams. Thus, data acquired during sequence number 5 again corresponds to color beam number 1, data acquired during sequence number 6 again corresponds to color beam number 2, and so forth.

After sequence number 40, each of the color beam numbers 1, 2, 3, and 4 includes data from ten respective (co-linear) Rx acoustic beams, which satisfies the packet size of ten. Because it takes approximately 250 μsec to acquire each data point (e.g., between each sequence), there is approximately 0.01 second between the sequence number 1 and the sequence number 40. During this time, data is respectively acquired for each of the color beam numbers 1, 2, 3, and 4 every 1,000 μsec (e.g., between sequence number 1 and sequence number 5), which corresponds to the color prf of 1 kHz.

After acquiring data for ten co-linear acoustic beams corresponding to each of the color beam numbers 1, 2, 3, and 4, the process repeats for color beam numbers 5, 6, 7, and 8. Then, the process continues for subsequent sets of four color beams until data for ten acoustic beams have been acquired for color beam number 40 (e.g., at sequence number 400).

As shown in FIG. 2, the sequence number 401 is the same as the sequence number 37 in that both acquire data corresponding to color beam number 1. However, the data from these two sequences may no longer be related because of the time interval between these two sequences. In other words, while data is added to color beam number 1 every 1,000 μsec between sequence number 1 and sequence number 37, a gap of approximately 91,000 μsec occurs between the sequence number 37 and the sequence number 401.

In contrast, certain embodiments disclosed herein acquire data continuously from multiple Rx beams (e.g., corresponding to different parallel scan lines or color beams) for each Tx beam. Thus, data may be acquired at a predetermined color sample rate without time gaps within a particular frame and/or between frames.

Figure 3:
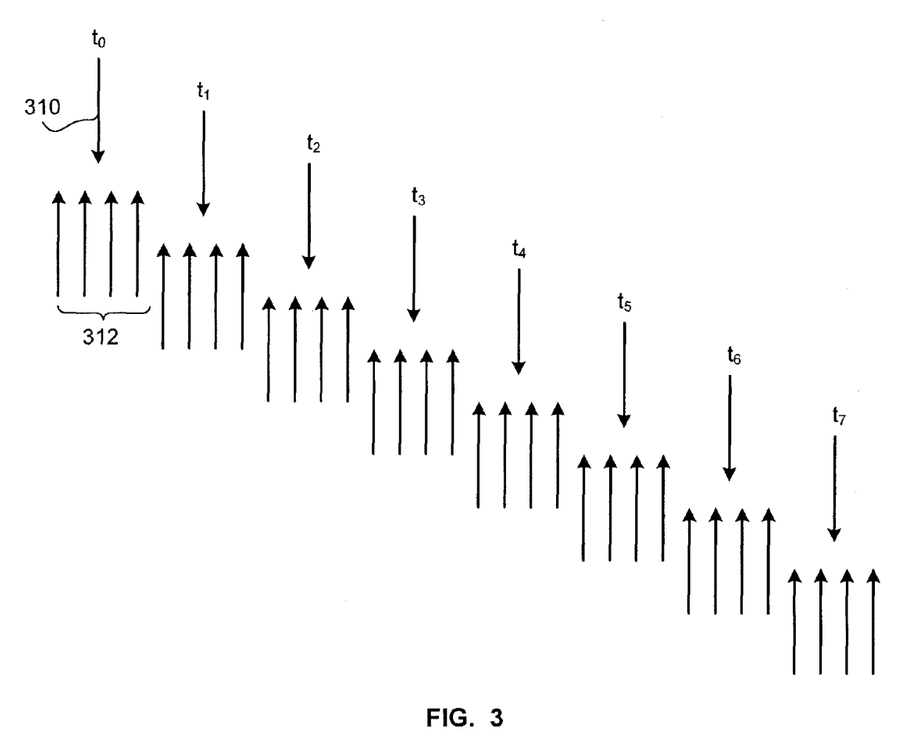
FIG. 3 is a graphical representation of a method according to one embodiment for transmitting and receiving acoustic beams to acquire color flow image data.

An ultrasound system according to one embodiment may form two, three, four or more Rx beams for each Tx beam. For example, FIG. 3 is a graphical representation of a method according to one embodiment for transmitting and receiving acoustic beams. As shown in FIG. 3, a single Tx beam 310 is transmitted and four Rx beams 312 are received at each sample time $t_0, t_1, t_2, t_3, \ldots, t_7$. Each of the four Rx beams 312 at a particular sample time may correspond to a different color beam. Although four Rx beams are shown in FIG. 3 for each Tx beam 310, one skilled in the art will recognize that different numbers of Rx beams 312 may be formed for each Tx beam 310 including, for example, eight, ten, twelve, fourteen, sixteen, eighteen, twenty or more Rx beams 312. Odd numbers of Rx beams 312 may also be formed for each Tx beam 310.

For the same example as that discussed above, the color data acquisition according to one embodiment is described below. In this embodiment, however, the system has a more powerful beamformer that is capable of receiving ten parallel Rx beams, for example, for every Tx beam.

Thus, for the same color image in the above case, color image data in one embodiment may be acquired according to the following sequence:

1. Tx1, Rx Color Beams 1-10;
2. Tx2, Rx Color Beams 11-20;
3. Tx3, Rx Color Beams 21-30;
4. Tx4, Rx Color Beams 31-40;
5. Tx5, Rx Color Beams 1-10;
6. Tx6, Rx Color Beams 11-20;
7. Tx7, Rx Color Beams 21-30;
8. Tx8, Rx Color Beams 31-40;
9. Tx9, Rx Color Beams 1-10;
10. Tx10, Rx Color Beams 11-20;
11. Tx11, Rx Color Beams 21-30;
12. Tx12, Rx Color Beams 31-40;
. . .

and so forth.

Figure 4:
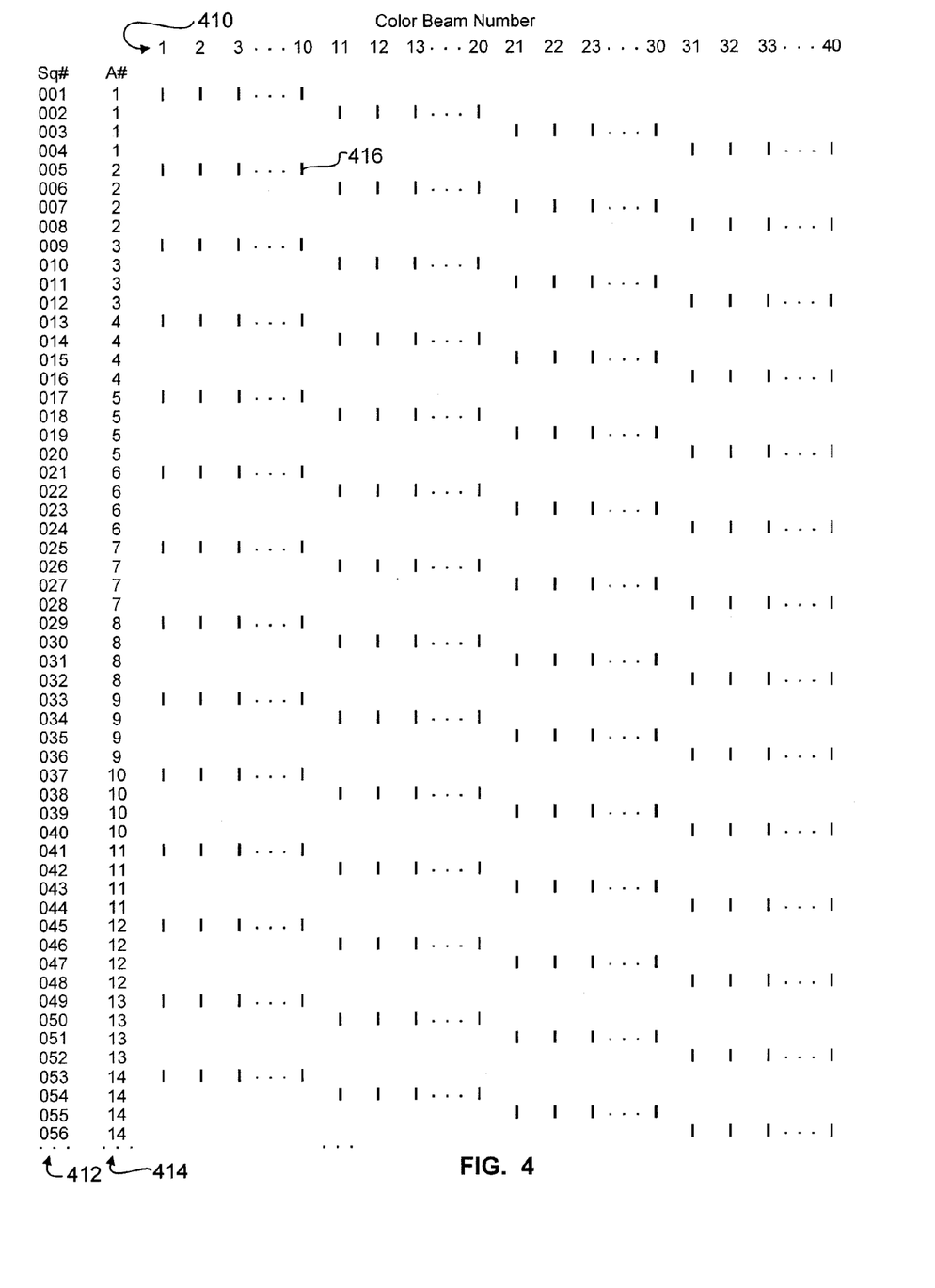
FIG. 4 is a graphical representation of sequencing used in color data acquisition according to one embodiment.

FIG. 4 is a graphical representation of sequencing used in color data acquisition according to one embodiment, and illustrates the sequencing listed above. The numbers in the horizontal row 410 represent the color beam numbers in a frame, which range from 1 to 40 in this example. The first column 412 represents the sequencing number (e.g., corresponding to sequential Tx/Rx beams, wherein multiple Rx beams are received for each Tx beam). The second column 414 represents the acoustic beam number order in a particular packet. In FIG. 4, the acoustic number within the frame is continuous because each color beam number 1 through 40 sequentially acquires data before repeating such that data is acquired at a predetermined color sample rate without time gaps within a frame and/or between frames. The lines 416 in the various rows and columns represent acquired acoustic data corresponding to respective sequence numbers and color beam numbers.

As shown in FIG. 4, data is acquired for ten color beams for each sequence. Thus, four Tx/Rx sequences provide data points for all forty color beams in the frame. Because each sequence is delayed from the previous sequence by approximately 250 μsec in this example (for an acoustic beam prf of 4 kHz), data is continuously added to each packet every 1000 μsec without gaps (either within the frame or between frames) in this rate. Thus, the color data is continuous at a color prf of 1 kHz (which is the color prf specified in the above example).

Figure 5:
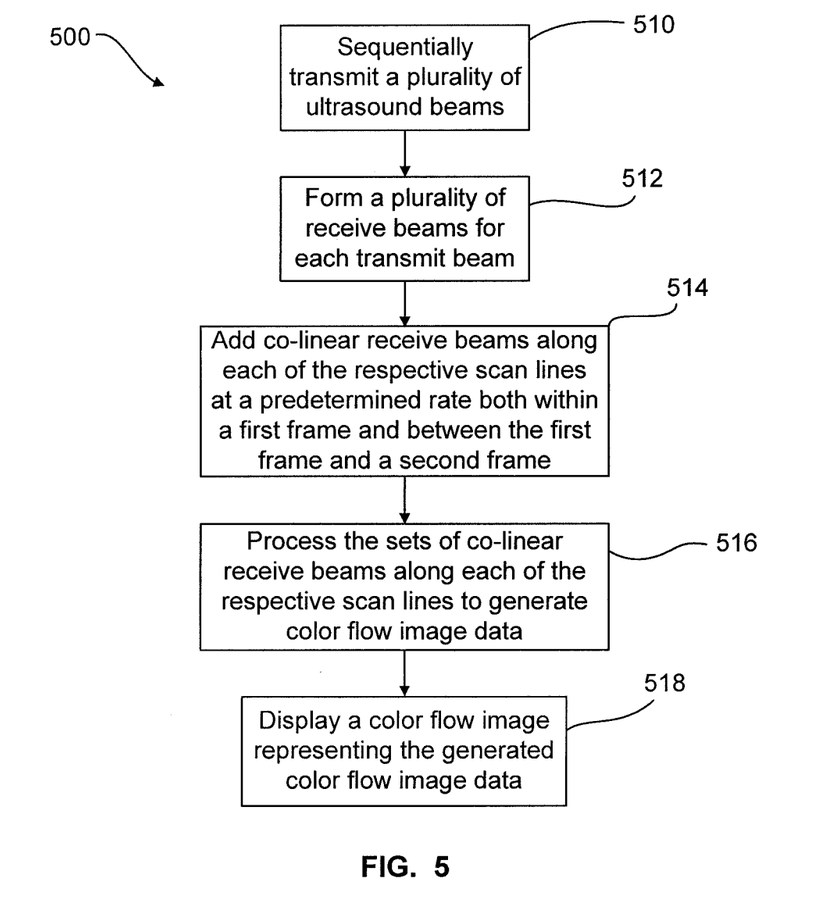
FIG. 5 is a flow chart illustrating a method for displaying ultrasound color flow image data according to one embodiment.

FIG. 5 is a flow chart illustrating a method 500 for displaying ultrasound color flow image data according to one embodiment. The method 500 includes sequentially transmitting 510 a plurality of ultrasound (Tx) beams, and forming 512 a plurality of Rx beams for each Tx beam. For example, as shown in FIG. 4, data 416 may be acquired for ten Rx beams corresponding to respective color beams for each Tx beam (e.g., represented by a respective sequence number in the first column 412). In one embodiment, data is added to each scan line (e.g., corresponding to color beam numbers 1-40 in FIG. 4) in a frame before adding additional data to any particular scan line.

The method 500 also includes adding 514 co-linear Rx beams along each of the respective scan lines at a predetermined rate both within a first frame and between the first frame and a second frame. For example, referring to FIG. 4, during sequence numbers 1 through 4, acoustic data 416 is added to each color beam number 1 through 40. Then, in sequence numbers 5 through 8, additional acoustic data 416 is added to each color beam number 1 through 40. Thus, after sequence number 8, each scan line includes data 416 from two co-linear Rx beams.

The method 500 also includes processing 516 the sets of co-linear Rx beams along each of the respective scan lines to generate color flow image data, and displaying 518 a color flow image representing the color flow image data.

In certain embodiments, the packet size is not predetermined by acoustic data acquisition. Rather, because the color data is continuous, the packet size is programmable in back end processing. Further, the packet size may be determined at a point in time after data acquisition. In addition, or in other embodiments, the color flow image frame rate is not determined by acoustic data acquisition. Rather, the color flow image frame rate may be programmable in back end processing.

Because the color sample rate is continuous, the color acoustic beam data may be used in more than one color frame. For example, referring to FIG. 4, if acoustic data 416 acquired during sequence numbers 1 through 16 are used for a first color frame (e.g., with a packet size of four), the acoustic data 416 acquired during at least sequence numbers 13 through 16 may also be used for a second color frame because there are no gaps in the color sample rate between sequence numbers 13 through 16 and sequence numbers 17 through 20, respectively. In other words, the data may be overlapped between frames.

Further, because the color sample rate is continuous, an ultrasound system according to certain embodiments may use a conventional method (e.g., a first order delay correlation) to compute the average velocity using the continuous data between frames. In addition, or in other embodiments, the ultrasound system may use the continuous data for fast Fourier transforms (FFT) to determine a velocity spectrum for each color pixel. In certain such embodiments, using the continuous data may greatly reduce the requirements of wall filter, key hole, smoothing, thresholding, and/or other signal processing operations. Thus, using the embodiments disclosed herein will make a revolution in medical color flow processing schemes.

For the embodiments described herein, the ultrasound system may process acquired color data for the trade off between time-resolution and the color sensitivity. To increase color sensitivity the system may use a larger packet size or a higher order FFT (e.g., a larger number of data points used in the FFT). To get more dynamic (time-resolution), the system may use a smaller packet or FFT size and less overlap.

The number of Rx beams used for each Tx beam may be user selected and/or automatically controlled by the ultrasound system according to certain embodiments. For example, in one embodiment, the number of Rx beams used for each Tx beam is a function of the depth desired to be imaged. As the depth increases, the number of Rx beams for each Tx beam may need to be decreased to maintain a desired prf. In one such embodiment, the system automatically determines the maximum number of Rx beams for each Tx beam based on the depth and the prf. In certain embodiments, the user may control the depth and/or the number of Rx beams. If the user determines that the frame rate is too slow at a selected depth, the user may change the number of Rx beams for each Tx beam. Thus, the user may manually adjust the frame rate for a particular depth and prf. In certain embodiments, the system may automatically change the number of Rx beams for each Tx beam to maintain a desired frame rate.

Using a large number of Rx beams for each Tx beams may cause acquired data for certain color beams to be weaker or less reliable. Thus, in some embodiments, the increased amount of continuous data in each packet may be averaged to reduce errors. In addition, or in other embodiments, relative positions of Tx and Rx beams may be changed so that the same color beams do not continuously receive weaker data while other color beams receive data that are more reliable. By overlapping Rx beams corresponding to different Tx beams, the errors may be reduced.

Figure 6:
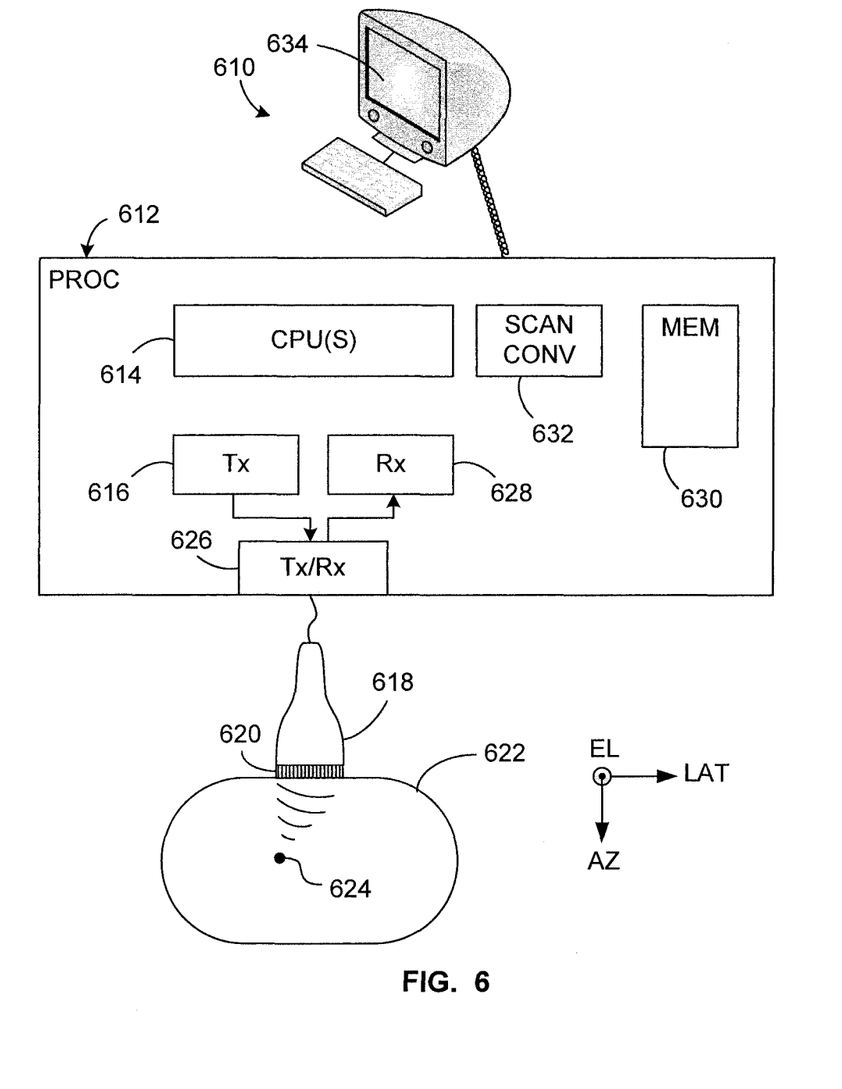
FIG. 6 illustrates certain components of an ultrasonic imaging system usable with the embodiments described herein.

FIG. 6 illustrates certain components of an ultrasonic imaging system usable with the embodiments described herein. The user enters various conventional scan parameters into an input/output (I/O) unit 610, which may comprise conventional hardware, system software, and devices such as a keyboard, knobs, a mouse, and/or buttons. The input unit is connected to a processing system 612, which will typically be an electrically connected and cooperating group of processors 614 such as microprocessors and digital signal processors with necessary system software such as, for example, an operating system. The I/O unit 610 may therefore not need any processing capability of its own but rather simply act as a peripheral device for the main processing system 612.

As in known systems, the processing system 612 sets, adjusts, and monitors the operating parameters of a conventional transmission control circuit 616. This control circuit 616 generates and applies electrical control and driving signals to an ultrasonic probe, that is, transducer 618, which includes an array 620 of electro-acoustic (usually piezoelectric, such as PZT) elements. As is well known in the art, piezoelectric elements generate ultrasonic waves when electrical signals of the proper frequency are applied to them.

To create the ultrasonic signals that are transmitted into the body (an "interrogation region," or a "region of interest" 622), all or some subset of these elements are electrically excited at a given frequency and are individually phased and time-shifted relative to each element's position in the array in such a way that the in-phase portions of the signals form a coherent transmit (Tx) beam. The time delays are chosen such that the echo signals arriving from a desired angular direction add coherently, whereas those signals arriving from other directions do not add coherently and so tend to cancel each other out. The amplitudes of the excitation signals applied to the array elements are typically varied (apodized) to control the resulting beam width and to suppress side lobes. The aperture of the array may also be varied, that is, the "width" of the activated elements (not all elements are usually activated at once) may be changed, just as the aperture of a camera may be varied to affect focal depth and provide uniform lateral resolution.

The various known methods for activating the elements according to a particular signal profile to best image a given area are generally referred to as transmit beamforming. By changing the amplitude and phasing of the transmitted signals, the Tx beam can be not only focused at a particular depth, but also steered off-axis, that is, not perpendicular to the center element among those activated. In FIG. 6, for example, the Tx beam has been steered at an angle to the face of the array 620. Out-of-phase portions of the individual transmit signals tend to cancel each other. The Tx beam typically converges at a focal depth, beyond which it once again diverges. The Tx beam is steered in the lateral direction LAT and/or the elevation direction EL; and is focused in the azimuth (axial) direction AZ so as to concentrate the ultrasonic energy of the beam onto desired points, such as a structure 624, within the interrogation region 622.

After any reflecting structure in the interrogation region is insonified, the transducer is typically switched by a switching circuit 626 from the transmit mode to a receive mode, such that the ultrasound reflected back onto the array face from any structures 624 within the imaged area will cause the elements to create corresponding electrical signals. The ultrasound sensed by any particular element, however, will be a combination of all the ultrasound energy reflected back from anywhere in the imaged region, regardless of which elements the energy originated from. In the general case, each element will receive some ultrasound energy created by all elements that were energized to form the Tx beam. In the receive (Rx) mode, each element will therefore generate a time-varying signal that in practice will differ from that of all other elements' received signals. Again, however, the in-phase portion of the reflected energy will dominate. The problem is how best to determine just what these coherent portions are, that is, which sensed values at the different elements represent the return signal from the desired focal point that, with proper time delay, corresponds to the portions of the return signals at the other array elements. This process is known as receive beamforming and a task of a receive beamformer is to determine and sum the coherent signals from targets received by all the active Rx array elements. A receive beamformer according to the embodiments disclosed herein includes separate channels for forming a plurality of Rx beams from echo signals in response to one Tx beam. Separate delays and/or apodization may be applied to each channel.

As is well understood, the piezoelectric array elements 620 convert the small mechanical vibrations caused by the echo signal into corresponding radio-frequency (RF) electrical signals. Amplification and other conventional signal conditioning are then applied to the return signals by a reception controller 628. This processing includes various procedures as needed to identify the echo signals that correspond to each scanned element in the interrogation region and form the Rx beam for each channel. The reception controller 628, all or part of which is normally integrated into the processing system 612 itself, also converts the ultrasonic, radio-frequency (RF) return signals (typically on the order of a few to tens of megahertz) into lower frequency ranges for processing. This is well known in the art of ultrasonic imaging. The reception control circuitry includes a receive beamformer, aspects of which are described in detail below. Note that the transmission and reception controllers (or, for that matter, the transmit and receive beamformers) do not have to be implemented as separate components but may be combined in whole or in part with respect to both their hardware and software.

In conventional B-mode scanning, each point within the interrogation region is then represented as an intensity (brightness) value. The interrogation region can therefore be represented as a discretized pattern (matrix) of brightness or signal intensity values, which are stored as frame data in a memory 630. Other scan modes, such as for Doppler imaging, create and store corresponding values.

The interrogation region is normally not in the same shape as what the user wants to see displayed; even when it is, the digital acoustic intensity values that make up the frame data are normally not in a form suitable for driving a conventional gray-tone or color display directly. The acoustic intensity values for a selected sub-set (scan plane) are then typically applied to a conventional scan converter 632, which converts the digital acoustic values into display intensity values that are suitable for use in driving a display device 634, which may be part of the I/O unit 610. The display device 634 typically includes a screen (for example, LED or CRT) that is divided into an X-Y (or polar) matrix or pattern of picture elements or "pixels" that make up an image that the user can view and interpret.

Figure 7:
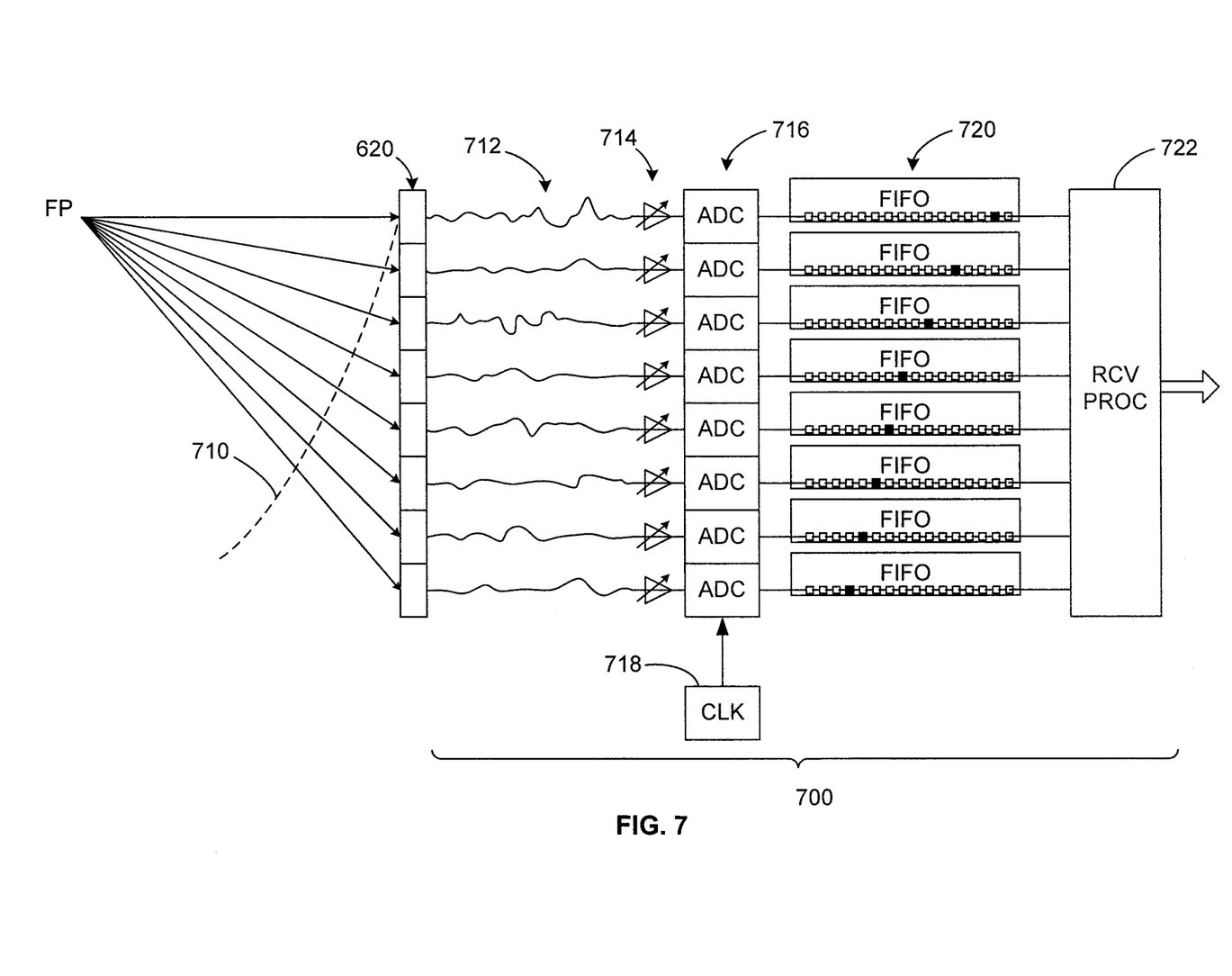
FIG. 7 illustrates certain components of a receive beamformer usable with the embodiments described herein.

FIG. 7 illustrates certain components of a receive beamformer 700 usable with the above-described embodiments. The illustrated beamformer 700 is simplified for purposes of illustration and the sizes and distances are not to scale. For example, even a one-dimensional linear array will usually have scores or even hundreds of array elements and not just the eight shown in FIG. 7. Moreover, it is common not to activate all the ultrasound elements at once, but rather to activate predetermined sub-sets of them according to some pattern. In FIG. 7, the Tx beam is assumed to have been focused on a focal point FP; the lines from the point FP back to the array elements represent the acoustic return signals, that is, the echoes of the transmitted ultrasound.

In the illustrated case, the focal point FP, for purposes of easy illustration only, lies perpendicular to the face of the uppermost array element. Assuming that the ultrasound is propagating through tissue that is at least substantially acoustically homogeneous, ultrasound energy of the Tx beam that is reflected back from the focal point FP will reach the uppermost array element before reaching the others. The dashed line 710 illustrates the travel of coherent ultrasound back towards the array elements 620; that is, line 710 illustrates the coherent portion of reflection of a Tx beam.

The reflected ultrasound causes each array element to generate a corresponding analog electrical signal 712. Usually after amplification by a bank of amplifiers 714, the analog signals 712 from the electro-acoustic array elements 620 are converted into digital values by a bank of analog-to-digital converters 716, whose sampling rate is controlled by clocking circuitry 718.

A time series of the converted digital values is then usually buffered in first-in-first-out latches 720 (for speed, although they could be stored in other types of memory devices). In FIG. 7, each stored digital value is represented as a small square on the signal path within the latches 720. The solid (filled in) squares within the latches 720 illustrate values corresponding to an echo from the same target.

The digital values are then processed in a processing module (722), which will generally involve the main processors 614 (FIG. 6) executing software code stored on a computer-readable medium. The software code defines not only the implemented beamforming routine, but also such procedures as may involve a dedicated processor part of the greater processor to form an output signal that represents the value to be assigned to the focal point, e.g., a brightness value. The processing will usually include such procedures as time-gating, gain compensation, diffraction compensation, dynamic receive delay, dynamic receive aperture size control, and dynamic receive apodization.

As discussed above, the digital ultrasound beamformer may generate one Tx beam, but receive multiple Rx beams back along respective scan lines. The beamformer may process these multiple beams by applying dynamic receive delay, dynamic receive aperture size control and dynamic receive apodization. The processing module 722 may process co-linear Rx beams along respective scan lines as described herein to generate color flow image data corresponding to the respective scan lines.

It will be understood by one skilled in the art that many changes may be made to the details of the above-described embodiments without departing from the underlying principles of the invention. The scope of the present invention, therefore, should be determined only by the following claims.

What is claimed is:

1. A method for displaying ultrasound color flow image data in a plurality of output color frames, each output color frame including a plurality of scan lines that collectively represent a field of view for an ultrasound image, the method comprising:
sequentially transmitting a plurality of ultrasound beams;
for each of the transmitted ultrasound beams, forming a plurality of receive beams along respective parallel scan lines, wherein sets of co-linear receive beams are formed at a predetermined rate within a first color frame which is equal to the rate at which sets of co-linear receive beams are formed between first and second color frames and equal to the rate at which sets of co-linear receive beams are formed within a second frame;

processing the sets of co-linear receive beams along each of the respective scan lines to generate color flow image data corresponding to the respective scan lines; and displaying a color flow image representing the generated color flow image data.

2. The method of claim 1, wherein forming the plurality of receive beams for each of the transmitted ultrasound beams comprises:

for a first transmitted ultrasound beam, forming a first predetermined number of receive beams corresponding to a first group of respective parallel scan lines; and for a second transmitted ultrasound beam, forming a second predetermined number of receive beams corresponding to a second group of respective parallel scan lines, wherein the second transmitted ultrasound beam is a next transmit beam following the first transmitted ultrasound beam in the sequentially transmitted plurality of ultrasound beams; and wherein the first group of respective parallel scan lines is different than the second group of respective parallel scan lines.

3. The method of claim 2, wherein forming the sets of co-linear receive beams comprises:

for a third transmitted ultrasound beam, forming a third predetermined number of receive beams corresponding to the first group of respective parallel scan lines such that the third predetermined number of receive beams are respectively co-linear with the first predetermined number of receive beams; and for a fourth transmitted ultrasound beam, forming a fourth predetermined number of receive beams corresponding to the second group of respective parallel scan lines such that the fourth predetermined number of receive beams are respectively co-linear with the second predetermined number of receive beams, wherein the first predetermined number of receive beams and the second predetermined number of receive beams are formed during a scan of a first color frame, wherein the third predetermined number of receive beams and the fourth predetermined number of receive beams are formed during a scan of a second color frame, and wherein a time between forming the first predetermined number of receive beams and forming the third predetermined number of receive beams is according to the predetermined rate.

4. The method of claim 1, further comprising:

after forming the receive beams corresponding to a particular color frame, determining the number of co-linear receive beams to include in each set for processing, wherein the determination is based on at least one of time-resolution and color flow sensitivity.

5. The method of claim 1, further comprising determining, without user intervention, the number of co-linear receive beams to include in each set for processing based on a depth of a point of interest imaged by the plurality of ultrasound beams.

6. The method of claim 5, further comprising automatically changing the number of co-linear receive beams to include in each set for processing so as to maintain a user-selected frame rate.

7. The method of claim 1, further comprising overlapping data between the first color frame and the second color frame, wherein at least one receive beam is processed along with a first set of co-linear receive beams to generate first color flow image data corresponding to the first color frame and along with a second set of co-linear receive beams to generate second color flow image data corresponding to the second color frame.

8. The method of claim 7, further comprising calculating an average velocity using first order delay correlation with data from both the first set and the second set.

9. The method of claim 7, further comprising calculating a velocity spectrum using a fast Fourier transform (FFT) with data from both the first set and the second set.

10. The method of claim 9, further comprising changing the number of receive beams from at least one of the first set and the second set that are used to calculate the FFT based on at least one of a time-resolution and a color sensitivity.

11. A system for displaying ultrasound color flow image data in a plurality of output color frames, each output color frame including a plurality of scan lines that collectively represent a field of view for an ultrasound image, the system comprising:

an ultrasound probe comprising an array of electro-acoustic elements;

a beamforming system comprising:

a transmit beamformer to sequentially transmit a plurality of ultrasound beams; and a receive beamformer to form, for each of the transmitted ultrasound beams, a plurality of receive beams along respective parallel scan lines, wherein sets of co-linear receive beams are formed along each of the respective scan lines continuously at a predetermined rate that is maintained both within a first color frame and between the first color frame and a second color frame, wherein the sets of co-linear receive beams are formed sequentially without overlap before repeating;

a processing system comprising at least one processor and at least one memory, the processing system to process the sets of co-linear receive beams along each of the respective scan lines to generate color flow image data corresponding to the respective scan lines; and a display system comprising a color monitor to display a color flow image representing the generated color flow image data.

12. The system of claim 11, wherein the receive beamformer forms the plurality of receive beams for each of the transmitted ultrasound beams by:

for a first transmitted ultrasound beam, forming a first predetermined number of receive beams corresponding to a first group of respective parallel scan lines; and for a second transmitted ultrasound beam, forming a second predetermined number of receive beams corresponding to a second group of respective parallel scan lines, wherein the second transmitted ultrasound beam is a next transmit beam following the first transmitted ultrasound beam in the sequentially transmitted plurality of ultrasound beams; and wherein the first group of respective parallel scan lines is different than the second group of respective parallel scan lines.

13. The system of claim 12, wherein the receive beamformer forms the sets of co-linear receive beams by:

for a third transmitted ultrasound beam, forming a third predetermined number of receive beams corresponding to the first group of respective parallel scan lines such that the third predetermined number of receive beams are respectively co-linear with the first predetermined number of receive beams; and for a fourth transmitted ultrasound beam, forming a fourth predetermined number of receive beams corresponding to the second group of respective parallel scan lines such that the fourth predetermined number of receive beams are respectively co-linear with the second predetermined number of receive beams, wherein the first predetermined number of receive beams and the second predetermined number of receive beams are formed during a scan of a first color frame, wherein the third predetermined number of receive beams and the fourth predetermined number of receive beams are formed during a scan of a second color frame, and wherein a time between forming the first predetermined number of receive beams and forming the third predetermined number of receive beams is according to the predetermined rate.

14. The system of claim 11, wherein the at least one processor is further configured to:

after forming the receive beams for a particular color frame, determine the number of co-linear receive beams to include in each set for processing, wherein the determination is based on at least one of time-resolution and color flow sensitivity.

15. The system of claim 11, wherein the at least one processor is further configured to determine, without user intervention, the number of co-linear receive beams to include in each set for processing based on a depth of a point of interest imaged by the plurality of ultrasound beams.

16. The system of claim 15, wherein the at least one processor is further configured to automatically change the number of co-linear receive beams to include in each set for processing so as to maintain a user-selected frame rate.

17. The system of claim 11, wherein the at least one processor is further configured to overlap data between the first color frame and the second color frame, wherein the at least one processor processes at least one receive beam along with a first set of co-linear receive beams to generate first color flow image data corresponding to the first color frame and along with a second set of co-linear receive beams to generate second color flow image data corresponding to the second color frame.

18. The system of claim 17, wherein the at least one processor is further configured to calculate an average velocity using first order delay correlation with data from both the first set and the second set.

19. The system of claim 17, wherein the at least one processor is further configured to calculate a velocity spectrum using a fast Fourier transform (FFT) with data from both the first set and the second set.

20. The system of claim 19, wherein the at least one processor is further configured to change the number of receive beams from at least one of the first set and the second set that are used to calculate the FFT based on at least one of a time-resolution and a color sensitivity.

* * * * *